United States Patent [19]

Sipilä et al.

[11] Patent Number: 4,520,267
[45] Date of Patent: May 28, 1985

[54] METHOD AND APPARATUS FOR ANALYZING ORE BY MEANS OF GAMMA RADIATION

[75] Inventors: Heikki Sipilä ; Erkki Kiuru; Seppo Vaijärvi, all of Espoo, Finland

[73] Assignee: Outokumpu Oy, Helsinki, Finland

[21] Appl. No.: 301,196

[22] Filed: Sep. 11, 1981

[30] Foreign Application Priority Data

Sep. 15, 1980 [FI] Finland .................................. 802882

[51] Int. Cl.³ ............................................. G01N 23/00
[52] U.S. Cl. ..................................... 250/358.1; 378/88
[58] Field of Search ................. 250/255, 358.1, 359.1, 250/360.1; 378/53, 69, 88

[56] References Cited

U.S. PATENT DOCUMENTS

| | | | |
|---|---|---|---|
| 4,090,074 | 5/1978 | Watt et al. | 378/88 |
| 4,314,155 | 2/1982 | Sowerby | 378/88 |
| 4,359,639 | 11/1982 | Wykes et al. | 250/255 |

Primary Examiner—Janice A. Howell
Attorney, Agent, or Firm—Brooks Haidt Haffner & Delahunty

[57] ABSTRACT

Disclosed is a method and an apparatus for analyzing pieces of ore for the purpose of sorting. Each piece falling by the analyzer is irradiated individually by means of two gamma radiation sources operating at different energy levels so selected that, as to the scattering effect, at one level the Compton effect is predominant and at the other level the Compton effect and the photoelectric effect compete with each other. The former effect is strongly dependent on the ordinal number of the element and, thus, by detecting with at least one detector the scattering intensities produced with the said two sources of radiation and comparing the scattering intensities with each other, the proportion of heavy elements in the ore piece can be determined and the ore piece can be classified on the basis thereof. For example, one energy dispersively operating scintillation detector can be used for detecting the scattered radiation.

10 Claims, 5 Drawing Figures

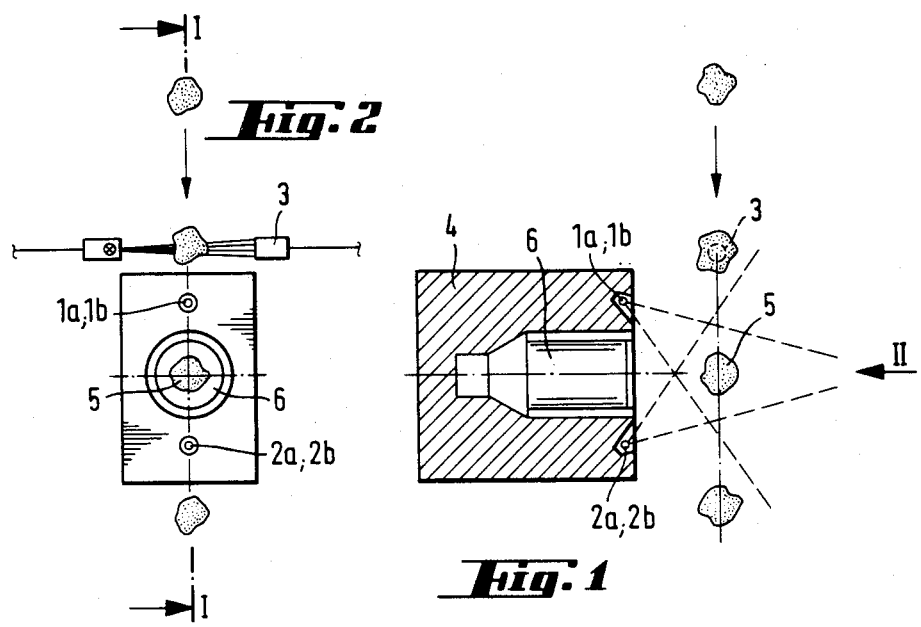
Fig. 2
Fig. 1
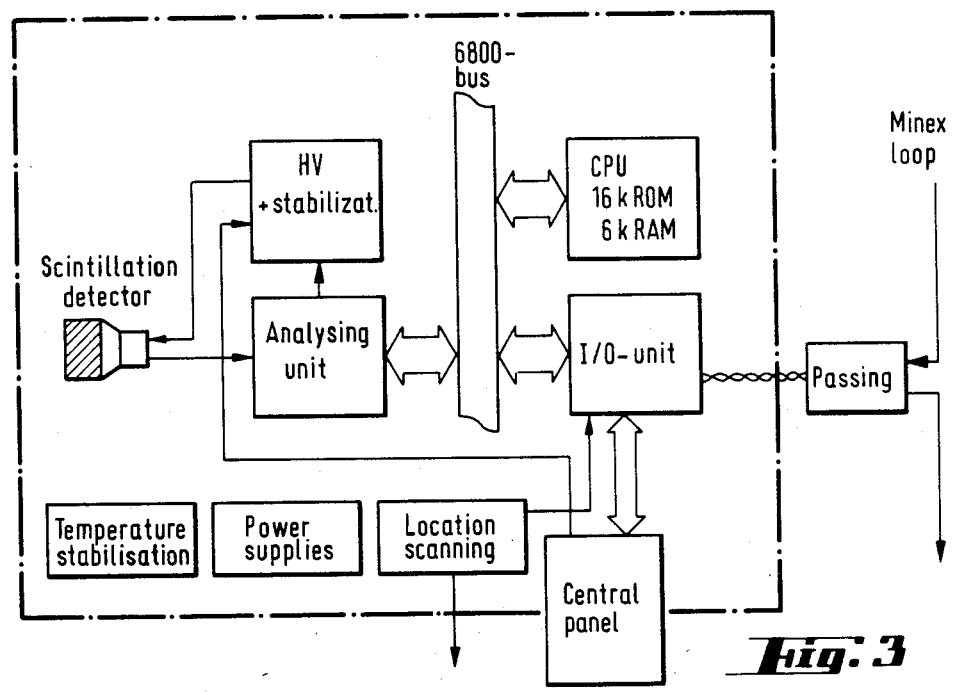
Fig. 3

METHOD AND APPARATUS FOR ANALYZING ORE BY MEANS OF GAMMA RADIATION

BACKGROUND OF THE INVENTION

1. Field of the Invention

The present invention relates to a method and apparatus for analysing, for the purpose of sorting, pieces of ore, a method wherein the fragments are irradiated individually by γ-radiation and the radiation scatter produced by them is examined.

2. Description of the Prior Art

It is previously known to use γ-radiation for the analysis of individual pieces of ore before they are transported for further treatment. However, since the size, dustiness, etc., of the pieces vary, it has been difficult to achieve sufficient precision in sorting. In order to improve the precision, it is known to use the capture-gamma method and a semiconductor detector, which has a good resolution capability but is expensive and requires special measures to shield it from damaging radiation.

SUMMARY OF THE INVENTION

The object of the present invention is to provide an analysing method based on γ-radiation, a method which with a relatively simple apparatus produces a good analysis result which is reliable in spite of variation of conditions.

To achieve this object, the invention provides a method of the character once described, which comprises irradiating the pieces individually by means of two gamma radiation sources, each operating at a different energy level, the energy levels of the sources having been selected so that, as to scattering, in one the Compton effect is predominant and in the other the Compton effect and the photoelectric effect compete with each other, the former being strongly dependent on the ordinal number of the element; and detecting by means of at least one detector the intensities of the scatter produced from said piece by the said two sources of radiation and compared the detected intensities with each other in order to determine the proportion of heavy elements present in the piece.

Thus, that which is essential in the invention is the use of two sources of radiation, each having a different level of energy. The use of such sources of radiation is a simple method for eliminating variations in the parameters of the pieces, such as the size and the purity, as well as variation in the background radiation.

The invention is described below in greater detail in the form of an example and with reference to the accompanying drawings.

An apparatus for analysing a piece of ore by means of gamma radiation comprises, according to the invention, two sources of gamma radiation, each operating at a different energy level, the sources of radiation being fitted to irradiate the piece substantially simultaneously and their levels of energy being selected so that in the scatter of the radiation the Compton effect is predominant at one energy level and the Compton effect and the photoelectric effect compete with each other at the other energy level, a detector for detecting the scatter produced by the radiations, said detector being situated so that it receives substantially only radiation scattered from the piece, and measuring means connected to the detector and adopted to compare with each other the intensities of the scatters produced by the two sources of radiation.

BRIEF DESCRIPTION OF THE DRAWINGS

FIG. 1 depicts diagrammatically a side view of a measuring arrangement according to the invention, FIG. 2 depicts an end view of the same arrangement, FIG. 3 depicts, in the form of a block diagram, the electronics unit connected with an apparatus according to the invention.

DESCRIPTION OF THE PREFERRED EMBODIMENT

Figure 4:
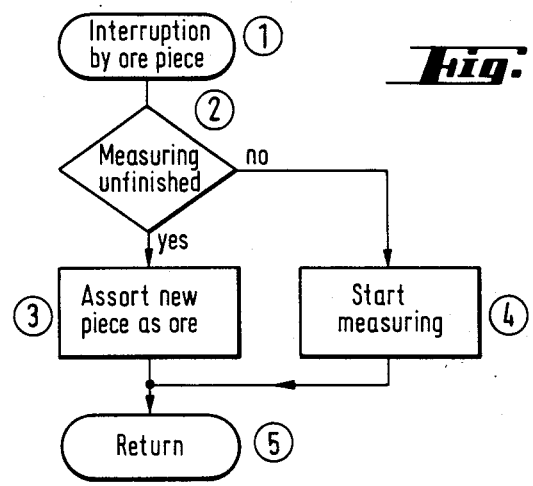
FIGS. 4 and 5 depict flow charts of the measuring procedure.

The geometry of the apparatus according to the invention is suitable as shown in FIG. 1. In it, two γ-radiation sources 1a, 1b, respectively 2a, 2b, each having a different level of energy, have been placed at substantially the same point, i.e. in the same indentation in the radiation shield 4. The reason for using two pairs of sources is that in this manner a stronger and more even radiation can be directed at the piece 5 falling by and being the object of the analysis. The energy level of the source of radiation 1a, respectively 2a, can be, for example, approx. 20–150 keV and the energy level of the source of radiation 1b, respectively 2b, can be approx. 300–1500 keV. In practice, sources of radiation Am-241 and Cs-137 have been used, their intensities being approx. 60 keV and approx. 600 keV.

Symmetrically in relation to the pairs of sources there is positioned a detector 6, which in this case is a scintillation detector the operation of which is energy dispersive.

In order to determine the initial point of the measuring, there is situated, somewhat above the source-detector combination, an ordinary photocell 3, which senses the arriving piece 5 when the piece cuts the ray of light between the source of light and the photocell.

Thus, the essential feature of the invention is that a piece of rock is irradiated by means of two γ-ray sources each having a different intensity of energy. The energy of one is selected so that the Compton effect is predominant. The energy of the other is selected so that the photoelectric effect and the Compton effect compete with each other. The photoelectric effect is strongly dependent on the ordinal number of the element, whereas the Compton effect is independent of the ordinal number. By measuring the ratio of the intensities of these two scatters having different levels of energy, a quantity is obtained which represents the proportion of heavy elements in the rock. In many cases, ore and dead rock can be very clearly distinguished from each other. The shape and the size of the piece of rock has hardly any effect on the result. The energies of the radiations can be selected so that the penetration is sufficiently high to prevent dirt on the surface of the rock from affecting the result.

FIG. 3 depicts the electronics unit of the analyser in the form of a block diagram. The essential feature of the system is that the intensity I, respectively II, of the scattered radiation is measured, by means of an energy dispersive detector, for each source (1a, 2a and 1b, 2b). The respective background intensities $I_o$ and $II_o$ are subtracted from these values, and finally the ratio of the differences is formed $$T=(I-I_o)/(II-II_o)$$

which is used as the result value of the analysis preformed. In a normal case the quantity T represents the proportion of a heavy element or heavy elements in the piece.

Figure 5:
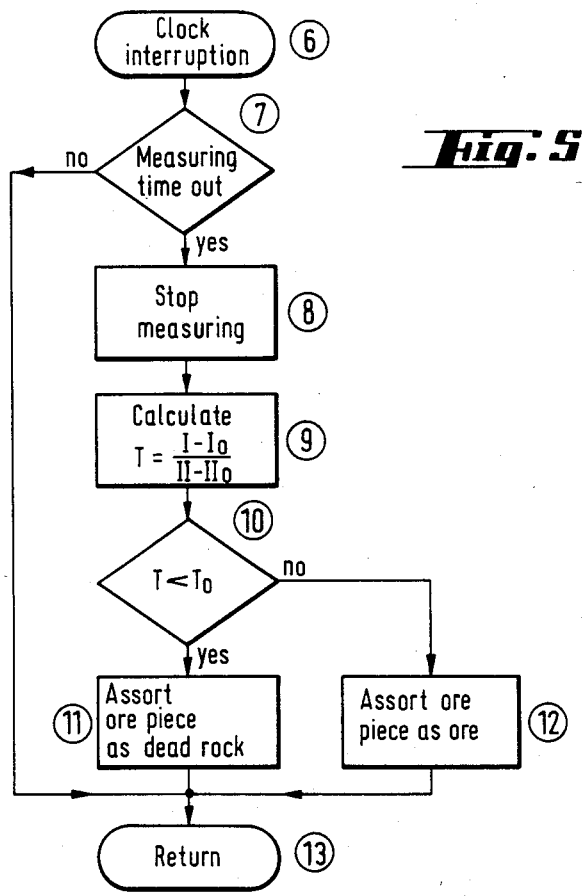

FIGS. 4 and 5 show flow charts of the operation of the analyser.

The chart of FIG. 4 depicts a situation which begins when a new piece of rock arrives in the measuring area. For the sake of simplicity, the procedure is such that, if the measuring of the previous piece is still continuing, the new piece is sorted as ore.

The timer interruption depicted in FIG. 5 is carried out at intervals of 1 ms. The above-mentioned test quantity T is formed in the analyser, and this quantity T is compared with the sorting threshold $T_o$ which is in the memory, and it determines the sorting of the piece as either dead rock of ore.

We claim:

1. A method for analysing pieces of ore for the purpose of sorting, comprising
   irradiating the pieces individually by means of two gamma radiation sources, each operating at a different energy level, the energy levels of the sources having been selected so that, as to scattering, in one the Compton effect is predominant and in the other the Compton effect and the photoelectric effect compete with each other, the photoelectric effect being strongly dependent on the ordinal number of each element present in the ore; and
   detecting by means of at least one detector the intensities of the scatter produced from said piece by the said two sources of radiation and comparing the detected intensities with each other in order to determine the proportion of heavy elements present in the piece.

2. A method according to claim 1, wherein the ratio (T) of two quantities is taken as a parameter representing the result of the sorting, the first quantity being the intensity (I) of the scatter produced by the first source, minus the intensity ($I_o$) of the background radiation, and the second quantity being the intensity (II) of the scatter produced by the second source, minus the intensity ($II_o$) of the respective background radiation.

3. A method according to claim 1, wherein the detector used is one scintillation detector operating energy dispersively.

4. A method according to claim 1, wherein the energy levels of the sources of radiation are within the range of approximately 20-150 keV and approximately 300-1500 keV.

5. An apparatus for analysing a piece of ore by means of gamma radiation, for the purpose of sorting, comprising two sources of gamma radiation, each operating at a different energy level, the sources of radiation being fitted to irradiate the piece substantially simultaneously and their levels of energy being selected so that in the scatter of the radiation the Compton effect is predominant at one energy level and the Compton effect and the photoelectric effect compete with each other at the other energy level,
   a detector for detecting scatter produced by the radiations, said detector being situated so that it receives substantially only radiation scattered from the piece and measuring means connected to the detector for comparing with each other intensities of the scatters produced by the two sources of radiation.

6. An apparatus according to claim 5, wherein the sources of radiation are situated at substantially the same point.

7. An apparatus according to claim 5, wherein the detector is a scintillation detector.

8. An apparatus according to claim 5, wherein the detector is connected to an electronic analysing circuit which comprises a pulse height analyser and a microprocessor linked to the analyser.

9. A method for analysing pieces of ore for the purpose of sorting, comprising
   irradiating the pieces individually by means of two similar pairs of gamma radiation sources, each of said pairs of sources comprising sources operating at different energy levels, the energy levels of the sources having been selected so that, as to scattering, in one the Compton effect is predominant and in the other the Compton effect and the photoelectric effect compete with each other, the photoelectric effect being strongly dependent on the ordinal number of each element present in the ore; and
   detecting by means of at least one detector positioned symmetrically between the pairs of sources the intensities of the scatter produced from said piece by said two sources of radiation of both pairs of sources and comparing the detected intensities with each other in order to determine the proportion of heavy elements present in the piece.

10. An apparatus for analysing a piece of ore by means of gamma radiation, for the purpose of sorting, comprising two similar pairs of sources of gamma radiation, each of said pairs of sources comprising two sources operating at different energy levels, the sources of radiation being fitted to irradiate the piece simultaneously and their levels of energy being selected so that in the scatter of the radiation the Compton effect is predominant at one energy level and the Compton effect and the photoelectric effect compete with each other at the other energy level,
   a detector positioned symmetrically between said pairs of sources for detecting scatter produced by the radiations, said detector being situated so that it receives substantially only radiation scattered from the piece and measuring means connected to the detector for comparing with each other intensities of the scatters produced by the two sources of radiation of both pairs of sources.

* * * * *